United States Patent
Hansen

(10) Patent No.: US 9,089,447 B2
(45) Date of Patent: Jul. 28, 2015

(54) INTRODUCER ASSEMBLY

(75) Inventor: Palle M. Hansen, Bjaeverskov (DK)

(73) Assignee: Cook Medical Technologies LLC, Bloomington, IN (US)

( * ) Notice: Subject to any disclaimer, the term of this patent is extended or adjusted under 35 U.S.C. 154(b) by 363 days.

(21) Appl. No.: 13/264,283

(22) PCT Filed: Apr. 16, 2010

(86) PCT No.: PCT/US2010/031413
§ 371 (c)(1),
(2), (4) Date: Nov. 3, 2011

(87) PCT Pub. No.: WO2010/121145
PCT Pub. Date: Oct. 21, 2010

(65) Prior Publication Data
US 2012/0041536 A1    Feb. 16, 2012

Related U.S. Application Data

(60) Provisional application No. 61/212,836, filed on Apr. 16, 2009.

(51) Int. Cl.
*A61F 2/06* (2013.01)
*A61F 2/95* (2013.01)
*A61F 2/07* (2013.01)

(52) U.S. Cl.
CPC ... *A61F 2/95* (2013.01); *A61F 2/07* (2013.01); *A61F 2002/9517* (2013.01)

(58) Field of Classification Search
CPC ..... A61F 2002/9517; A61F 2/07; A61F 2/95; A61F 2/966
USPC ............ 623/1.11, 1.12, 1.23; 128/898; 604/164.01, 164.08, 164.13, 164.1, 604/164.05, 167.03, 264, 158, 171, 528, 604/535, 523, 165.01, 104; 600/585; 606/198, 191, 108, 194
See application file for complete search history.

(56) References Cited

U.S. PATENT DOCUMENTS 5,980,553 A   11/1999   Gray et al.
7,331,985 B2   2/2008   Thompson et al.
(Continued)

FOREIGN PATENT DOCUMENTS

EP          0 747 021 A2     6/1996
WO     WO 2006/117167 A1    11/2006
WO     WO 2009/013642 A1     1/2009

OTHER PUBLICATIONS

Search Report for related PCT Application No. PCT/US2010/31413, mailed Aug. 23, 2010.

*Primary Examiner* — Kathleen Holwerda
*Assistant Examiner* — Jocelin Tanner
(74) *Attorney, Agent, or Firm* — Brinks Gilson & Lione

(57) ABSTRACT

An introducer assembly (40) for use in the deployment of implantable medical devices such as stents and stent grafts includes a carrier element (20), a dilator tip (18) located at the distal end of the carrier element (40) and sheath (32) movable between a device covering position and a device deployment position. In the device deployment position, a restricted annular gap (34) is created between the distal end (36) of the sheath (32) and the proximal end (38) of the dilator tip (18). The gap (34) is restricted by a restriction mechanism (50) located at the proximal, external end, of the introducer assembly (40). The gap (34) allows for the progressive deployment of the medical device from the introducer (40) and for simultaneous retraction of the dilator tip (18) thereby avoiding snagging of the dilator tip (18) against the wall of a patient's vessels and of the medical device.

33 Claims, 7 Drawing Sheets

(56) References Cited

U.S. PATENT DOCUMENTS

| | | | |
|---|---|---|---|
| 2002/0029076 A1* | 3/2002 | Yee | 623/1.11 |
| 2006/0155357 A1 | 7/2006 | Melsheimer | |
| 2006/0184226 A1 | 8/2006 | Austin | |
| 2007/0088368 A1 | 4/2007 | Acosta et al. | |
| 2007/0123971 A1* | 5/2007 | Kennedy et al. | 623/1.11 |
| 2008/0288043 A1* | 11/2008 | Kaufmann et al. | 623/1.11 |

* cited by examiner

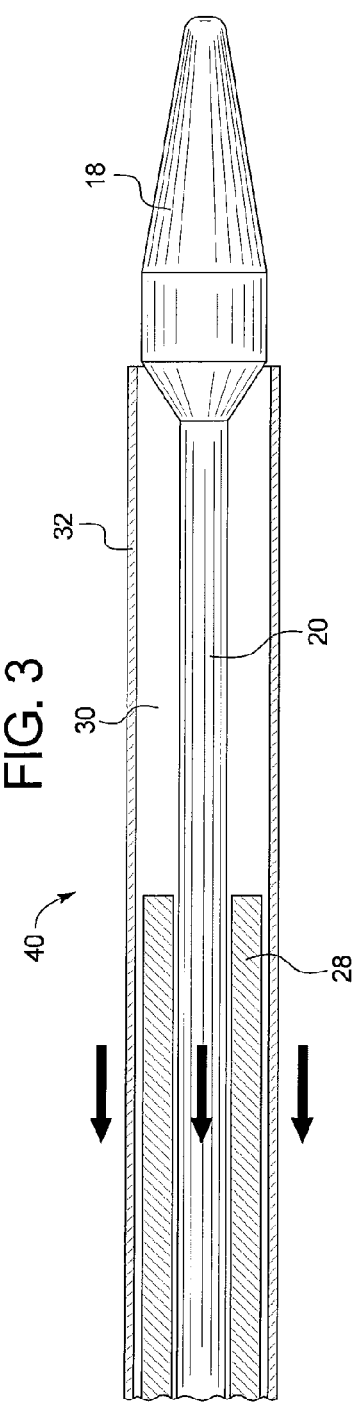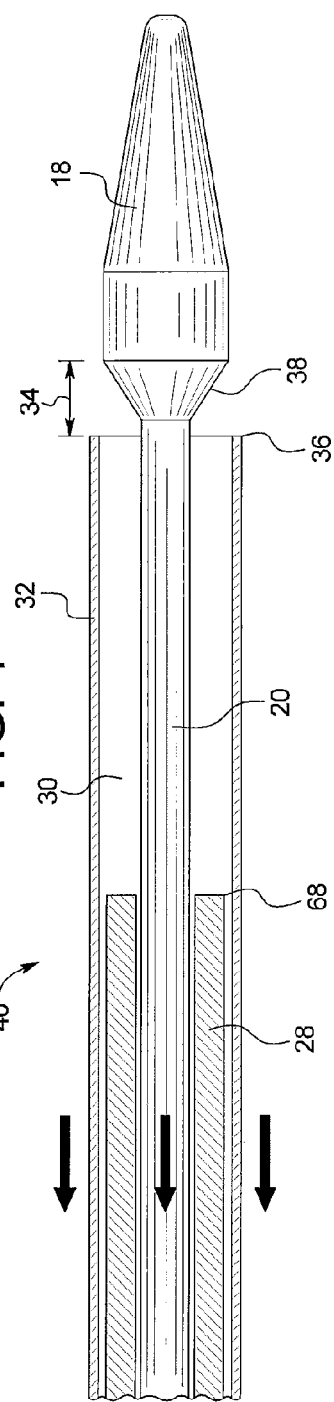

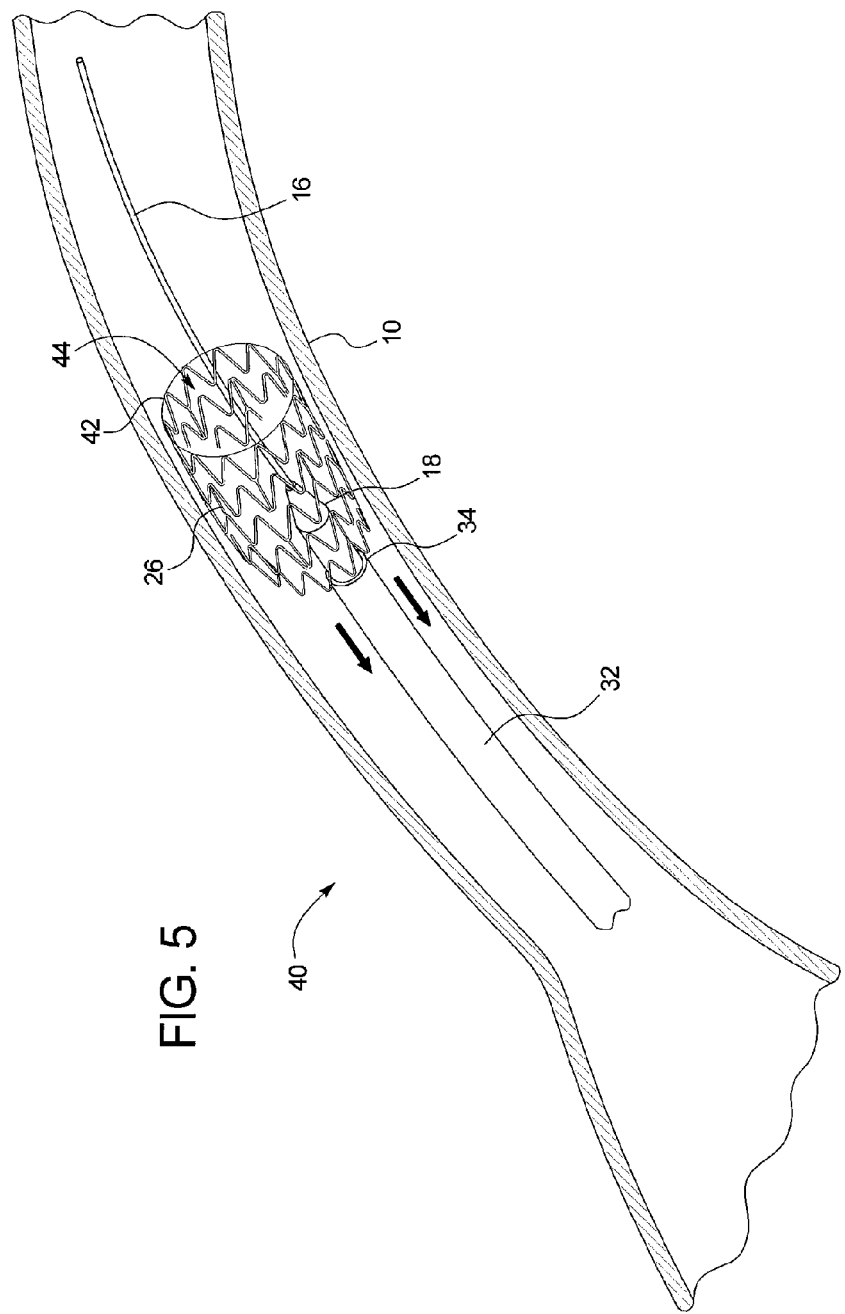

INTRODUCER ASSEMBLY

This application is a National Stage of International Application PCT/US2010/31413 filed Apr. 16, 2010, which claims the benefit of the filing date under 35 U.S.C. §119(e) of Provisional U.S. Patent Application Ser. No. 61/212,836, filed Apr. 16, 2009. The entirety of both applications is hereby incorporated by reference.

TECHNICAL FIELD

The present invention relates to an introducer assembly for use in the endoluminal deployment of implantable medical devices such as stents, stent grafts and other devices.

BACKGROUND OF THE INVENTION

The endoluminal introduction and deployment of a medical device such as a stent or stent graft into a patient is a well known procedure. The introducer assembly is typically in the form of a catheter assembly which includes at least guide wire, a guide wire catheter and an outer sheath. The medical device is carried at a distal end of the guide wire catheter and the assembly may also include a pusher element which is also carried on or is part of the guide wire catheter. It is advantageous to have a flexible distal end to the introducer to assist in its trackability within the vasculature of a patient. It is also advantageous for the distal tip of the introducer to have a dilating function so as to prepare the lumen for the passage of the larger sheath-covered part of the assembly. For this purpose it is generally considered best to have a specific dilator tip at the distal end of the introducer assembly, formed of a very flexible material. The implantable medical device is typically positioned just by the proximal end of the dilator tip and on a cannula or catheter which has a smaller outer diameter than the diameter of the dilator tip.

During deployment, the implantable medical device is expanded from the introducer until this fixes to the inner walls of the patient's lumen at the treatment site. Once deployed, the introducer is removed, typically by withdrawing the guide wire catheter through the lumen of the expanded medical device. The dilator tip also follows through the lumen of the medical device. This withdrawal operation generally occurs without complications. However, where the medical device is deployed in a curved vessel, such as in the aortic arch, it is possible for the distal end of the introducer assembly, particularly the dilator tip, to rub and pull against the internal surface of the medical device. The reason this occurs is that the introducer assembly will generally have a straight configuration, or at least much straighter than the curve of such a vessel, and as a result will tend to reside against or proximate the outer radial side of the lumen. Thus, when the introducer comes to be withdrawn, it will brush against this side of the vessel and the deployed medical device. In some circumstances this can cause damage or trauma to the vessel walls and or shift the device from the position in which it was deployed. There is also the risk of damage to the medical device. Any movement or damage to the device can lead to an abortive medical procedure.

WO-2006/117167 discloses an introducer for a self-expanding braided stent which includes a mechanism within the introducer assembly at its distal end for holding and controlling deployment of the stent.

U.S. Pat. No. 5,980,533, US-2006/0184226 and U.S. Pat. No. 7,331,985 disclose other designs of introducer assembly.

SUMMARY OF THE INVENTION

The present invention seeks to provide an improved introducer assembly for use in the endoluminal deployment of implantable medical devices such as stents, stent grafts and other devices.

According to an aspect of the present invention, there is provided an introducer assembly for use in the endoluminal deployment of an implantable medical device, the assembly including a distal end a proximal end; an elongate carrier element including a distal end and a proximal end and being operable to carry a medical device at or proximate its distal end; an elongate sheath operable to cover the carrier element and a medical device thereon, wherein the sheath is movable by a sliding action from a covering position covering a medical device carried on the introducer to a deployment position in which the medical device can be released from the introducer; and a restriction mechanism operable to restrict the amount of movement of the sheath relative to the carrier element such that the distal end of the carrier element is withdrawn simultaneously with expansion of a medical device carried on the introducer, the restriction mechanism being located at or proximate the proximal ends of the carrier element and sheath.

Withdrawing the distal end of the carrier element simultaneously with the process of expansion of the medical device causes the distal end to be located within the medical device itself as this is being released from the introducer. The partly deployed medical device acts to place in the centre thereof and to support the distal end of the introducer in the middle of the lumen of the medical device during the deployment/withdrawal operation. As a result, the risk of the distal end of the introducer scraping against the wall of the vessel or of the medical device are avoided or minimized.

In the preferred embodiment, the restriction mechanism is such as to provide a small annular gap through which the medical device can expand.

Locating the restriction mechanism at the proximal end of the introducer, typically so as always to remain outside the patient, ensures that this mechanism need not be designed so as to be insertable endoluminally, which would severely affect the size and form permissible for the restriction device, the types of vessel where it could be used and the performance of the introducer. Furthermore, the distal end of the introducer can be kept of relatively simple construction and one which does not alter the trackability or pushability characteristics of the introducer compared to existing devices.

Advantageously, the carrier element is a guide wire catheter, which allows for deployment by the Seldinger technique.

Preferably, the assembly includes a dilator tip at the distal end of the carrier element.

In one embodiment, the restriction mechanism includes a slide and follower coupled to a respective one of the carrier element and the sheath, the slide having a limited range of travel, at the end of which further sliding of the sheath relative to the carrier element is prevented. The slide may be in the form of a slot. In another embodiment, the slide is in the form of a guide rod.

The restriction element may provide for an annular gap to be opened at the distal end of the sheath which is wider than the thickness of the medical device carried on the introducer. In this embodiment, thus, the radial spacing between the carrier element and sheath is less than the width of the annular gap.

In another embodiment, the restriction element provides for an annular gap to be opened at the distal end of the sheath which has a width substantially the same as or slightly smaller than the thickness of the medical device carried on the introducer. In this embodiment, thus, the radial spacing between the carrier element and sheath is the same as or greater than the width of the annular gap. In this embodiment, the medical device will expand though the annular gap while contacting the surfaces of the sheath and dilator tip, which applies friction to the movement of the medical device, useful in reducing or preventing jerking of the medical device or introducer during the deployment operation.

BRIEF DESCRIPTION OF THE DRAWINGS

Embodiments of the present invention are described below, by way of example only, with reference to the accompanying drawings, in which:

FIG. 3 shows in schematic form and in partial cross-section the distal end of an embodiment of introducer;

FIG. 4 shows the distal end of the introducer of FIG. 3 with a sheath thereof in a withdrawn position;

FIG. 5 shows the distal end of the introducer of FIGS. 3 and 4 during an operation to deploy a stent held on the introducer;

DETAILED DESCRIPTION

Figure 1:
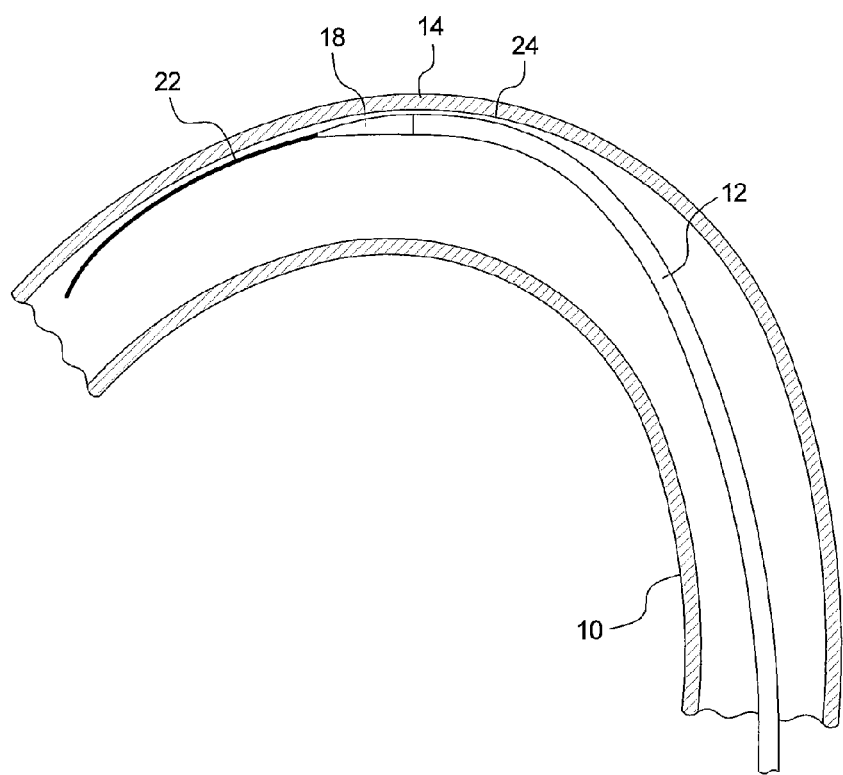
FIG. 1 shows in schematic form an example of introducer device located within a curved vessel.

Referring to FIG. 1, there is shown an example of a curved vessel 10 representing an aortic section which may have the dimensions and a curvature equivalent to that of the aortic arch of a human. Within the vessel 10 there is located an introducer 12, the distal end 14 of which is located at or around the zone of greatest curvature of the vessel 10. The tip of the introducer 10 is provided with a flexible dilator tip 18, of known form. The dilator tip 18 is fixed to the distal end of a guide wire catheter 20 (visible in FIG. 2). The introducer 12 and dilator tip 18 are provided with an internal lumen which receives a guide wire 22, also of conventional form, for assisting in guiding the insertion and movement of the introducer through a patient's vessels.

The typical procedure for introducing the introducer 12 into a patient is by means of the well known Seldinger technique, in which the guide wire 22 is first inserted percutaneously into a patient's vasculature via a needle which is then removed. The introducer assembly 12 is then inserted percutaneously and endoluminally into the patient, over the guide wire 22 which acts to guide the introducer assembly 12 through the vasculature up to the treatment site.

The introducer assembly 12 is generally of a straight or relatively straight configuration and is sufficiently flexible so as to follow the curvature of the vessels through which it passes, including highly curved vessels such as the vessel 10 shown in FIG. 1. Introducers 12 need to be generally straight in order to be trackable within the tortuous vessels of a patient.

When following the path of a curved vessel, such as vessel 10, the introducer 12 will be urged against the outer wall region 24 of the vessel 10 by virtue of the introducer's tendency to straighten, being curved only by the outer wall region 24 of the vessel imparting a curving force to the guide wire 22 and introducer 12.

Figure 2:
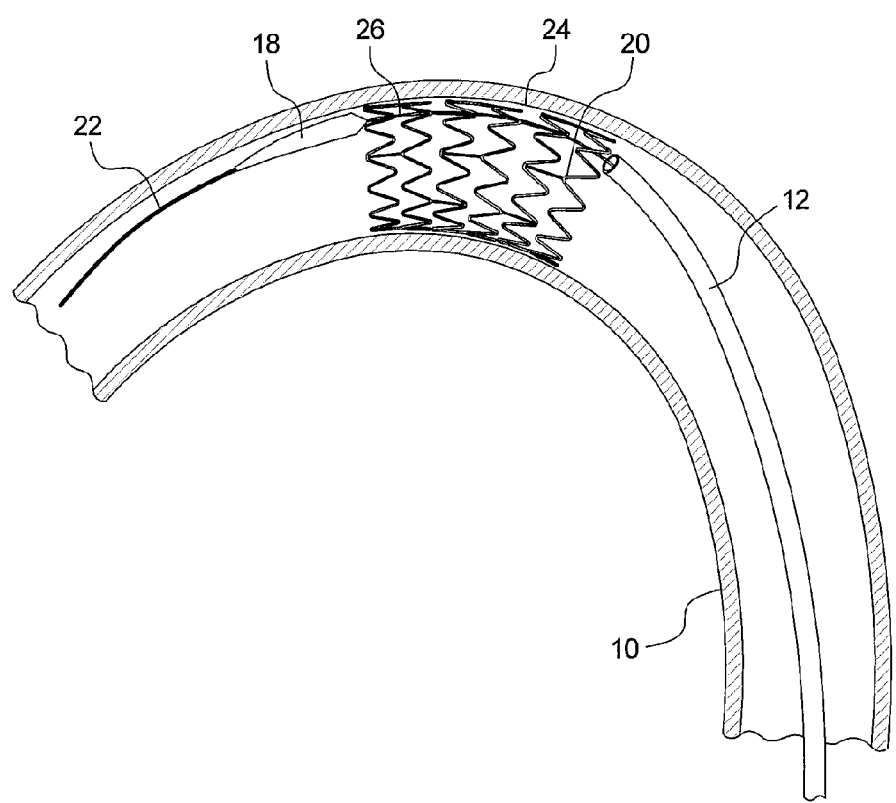
FIG. 2 shows the introducer of FIG. 1 once a stent held in the introducer has been deployed.

Referring now to FIG. 2, when the implantable medical device, in this example a stent 26, is released from the introducer assembly 12, the device will expand until it presses against the walls of the vessel 10, at which point it is fully deployed. Once the device 26 has been deployed and completely released from its ties to the introducer 12, the introducer 12 must be removed from the patient. This involves withdrawing the distal end of the assembly, including the guide wire 22, through and passed the deployed medical device 26 and then out of the patient. In most cases, the dilator tip 18 is also retracted to the position shown in FIG. 1 in which the sheath 12 covers the proximal end of the dilator tip 18.

As will be apparent from FIG. 2, since the dilator tip 18 will tend to be located at the outer wall region 24 of a curving vessel 10, as a result of the tendency of the introducer 12 to flex to its non-curved or less-curved configuration, there is a risk that during its retraction from the patient's vessel the dilator tip 18 will scrape against the vessel wall 24 and against the internal surfaces of the implantable medical device 26. Should this occur, there is a risk not only of damage to the vessel wall 24 but also a risk of damage to or displacement of the medical device 26. Any damage or displacement of the medical device 26 can result in an abortive procedure.

Referring now to FIGS. 3 and 4, there is shown the distal end of an embodiment of introducer 40. The introducer 40 is provided with a dilator tip 18 of conventional form coupled to a guide wire catheter 20, again of conventional form. The introducer 12 is also provided with a pusher rod or element 28, of known form, which is spaced from the proximal end of the dilator tip 18 to provide at the distal end of the guide wire catheter 20 a holding zone 30 which supports an implantable medical device, such as a stent 26. There may be provided at the holding zone 30 one or more restraining devices (not shown) for restraining the implantable medical device in a contracted configuration on the introducer. Such restraining devices may include restraining wires, cups and the like, of types known in the art.

A sheath 32 covers the guide wire catheter 20, the pusher element 28, the implantable medical device 26 carried on the introducer. The sheath 32 is movable from a covering configuration as shown in FIG. 3, in which the holding zone 30 and thus an implantable medical device held thereto are entirely covered by the sheath 32, to a deployment position as shown in FIG. 4. In the deployment position shown in FIG. 4, the sheath 32 has been retracted, in a proximal direction of the assembly 40, to open a gap 34 between the distal end of the sheath 32 and the proximal end of the dilator tip 18. This gap 34 is sufficient to provide an annular space between the distal end 36 of the sheath 32 and the proximal end 38 of the dilator tip 18 of limited width, in contrast to conventional introducer systems in which the sheath 32 is removed from the entirety of the medical device carrying zone 30 of the introducer.

The gap 34 extends only for a part of the length of the holding zone 30, preferably for just a minor part of this. In practice, the gap 34 provides an annular space between the distal end 36 of the sheath 32 and the proximal, conical, end 38 of the dilator tip 18. The dimensions of the gap 34 are between about the same as the thickness of the implantable medical device carried on the introducer 40 and may be slightly greater than this thickness. In other terms, the width of the gap is preferably about the same as or slightly larger than the radial spacing between the carrier catheter 20 and the inner side of the sheath 32. This gap thus allows the medical device through the gap only by this sliding through the gap, in contrast to prior art systems which provide for the sheath 32 to be retracted for substantially the entirety of the holding zone 30, typically more than this, to allow a purely radial expansion of the medical device from the introducer. The deployment mechanism of this embodiment is shown in better detail in FIG. 5.

Referring now to FIG. 5, there is shown the introducer of FIGS. 3 and 4 during a procedure to deploy a stent 26 within a vessel 10 of a patient. After location of the introducer 40 into the vessel 10, preferably by the Seldinger technique, the sheath 32 is retracted by the predetermined amount to open the annular gap 34 between the distal end 36 of the sheath 32 and the proximal, tapered end 38 of the dilator tip 18. In this embodiment, the pusher element 28 is then pushed forwards so as to assist in pushing the stent 26 through the gap 34, such that the proximal end 42 of the stent 26 passes through the gap 34 first. Typically, the tapered shape of the proximal end 38 of the dilator tip 18 will assist in guiding the proximal end 42 of the stent 26 out of the introducer 40 and in its expansion.

The introducer 40, that is the locked sheath 32 and distal tip 18 combination, is gradually retracted as the stent 26 is gradually released from the introducer 40 and deployed into the vessel 10. As can be seen in FIG. 5, the stent 26 progressively exits through the gap 34 and as it does so it expands gradually from the end of the introducer to engage the walls of the vessel. As the stent 26 is progressively deployed in this manner the dilator tip 18 moves with the sheath 32 in a proximal (downstream) direction, located always within the lumen 44 of the stent 26. The distal end of the introducer assembly 40 remains substantially centered within the lumen 10 during this procedure as it is supported and guided by the stent 26 as this expands.

Thus, it could be said that the introducer assembly 40 of the embodiments of FIGS. 3 to 5, including the sheath 32 and the guide wire catheter/dilator tip are retracted simultaneously with the deployment of the medical device carried on the introducer. This can be contrasted with the prior art assembly of FIG. 2, in which there is no such support for the distal end of the introducer assembly 12 and in particular of the dilator tip 18, as the prior art arrangement deploys the entirety of the medical device prior to withdrawal of the guide wire catheter and dilator tip. With the support and gradual retraction of the distal end of the introducer 40, there is little risk of the dilator tip 18 scraping or brushing against the walls of the vessel 10 or of the medical device 26 once this has been deployed.

As well as preventing unwanted contact between the distal end of the introducer 40 and the vessel or device walls, this effect of locating the distal end of the introducer 40 towards the centre of the lumen, as shown in FIG. 5, enhances the accurate placement of the medical device as this can expand and deploy from a central position in the lumen rather than from one side, as occurs with the prior art system of FIGS. 1 and 2.

Figure 6:
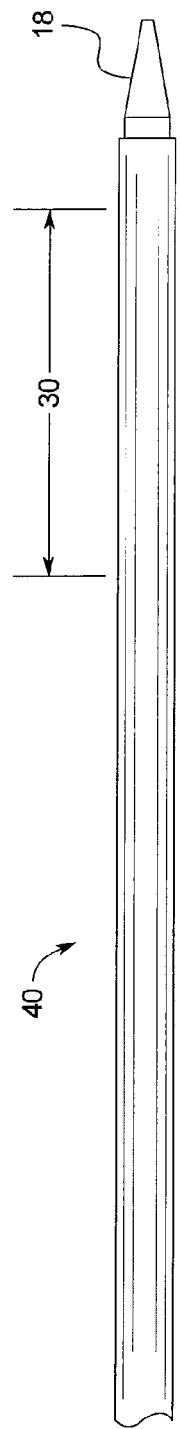
FIGS. 6 and 7 show the distal end of the introducer of FIGS. 3 and 4 in two different operating states.
Figure 7:
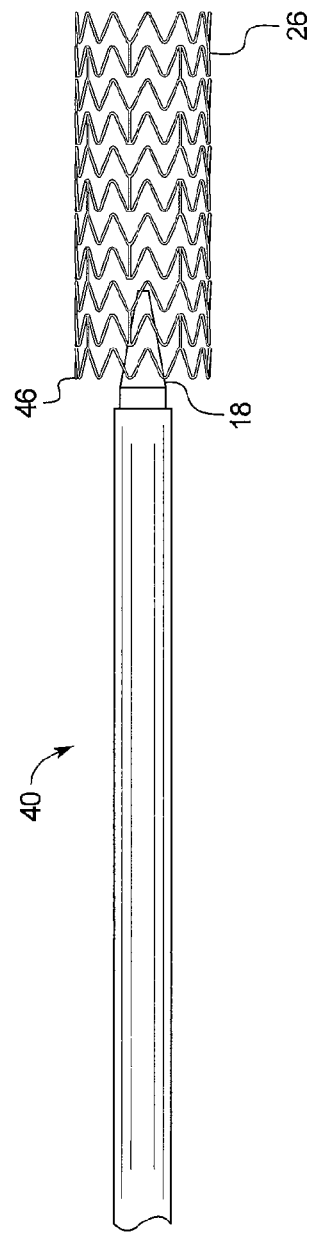

Referring now to FIGS. 6 and 7, there shown in schematic form the distal end of the introducer 40 prior to deployment of the medical device (FIG. 6) and just at the point at which the medical device has been deployed (FIG. 7). As can be seen in FIG. 7, at the moment of full deployment of the stent 26 the distal tip 18 has passed substantially entirely through the lumen of the medical device 26. In practice, its proximal end 38 will always be beyond the location of the distal end 46 of the medical device 26 at the moment at which this has been deployed. Thus, there is no or virtually no risk of snagging of the dilator tip 18 against the deployed medical device 26 in a manner which could cause damage to the medical device 26 or which might cause this to be unintentionally shifted from its deployed position.

In the preferred embodiment, the gap 34, which is of limited width as explained below, is only slightly greater than the thickness of the walls of the medical device 26, in the case of a stent, the thickness of the struts forming the stent, in the case of a stent graft, of the thickness of the combination of stent and graft at any point along the length of the stent graft. It is, however, envisaged also that the gap 34 could be slightly less than the thickness of the walls of the medical device. The sheath 32 and dilator tip 18 are typically made of a material with slight resiliency. Thus, when the gap 34 is of a dimension slightly less than the thickness of the walls of the medical device 26, the latter must be pushed through the gap 34 and that there will be some friction imparted to the medical device 26 as this is pushed through the gap. There are particular advantages to this arrangement. It is common for such medical devices, for example stents, stent grafts, filters and the like, to be made of a self-expanding material, such as Nitinol, spring steel or other shape memory material. Such devices have an inherent springiness which can cause them to jump from the introducer once they are released from their constraining mechanisms. Providing some form of holding the feature, such as the friction created by a gap 34 which is slightly less than the thickness of the walls of the medical device, can reduce any such sudden and jerky movements of the device as it is released from the introducer and can thus ensure more accurate placement of the medical device 26 within the vessel 10 of a patient. It will be appreciated that the gap 34 would be dimensioned so as to impart an adequate amount of friction to the medical device 26 without risking any damage or distortion to the device 26 which could impair its functionality or deployment and that these dimensions will be dependent upon the strength of the medical device and the resiliency of the distal end of the sheath 40 and/or the proximal end 28 of the dilator tip 18. These are parameters which are well within the ability of the skilled person to determine and are dependent upon the particular components used.

The dimensions of the gap 34, in particular of its width, can also be measured against the radial extent of the space between the carrier element 20 and the sheath 32. The medical device will typically have a wall thickness substantially the same as the radial extent of the annular holding zone 30. Thus, for a gap which is at least as large or larger than the thickness of the walls of the medical device, the gap 34 may have a width which is at least as large or greater than the radial spacing between the carrier 20 and the sheath 32, that is of the radial spacing of the annular holding zone 30. Similarly, for a gap 34 which is slightly narrower than the thickness of the walls of the medical device, the gap 34 could have a width which is less than the radial extent of the annular holding zone 30 or less than the radial gap between the carrier 20 and the sheath 32.

Figure 8A:
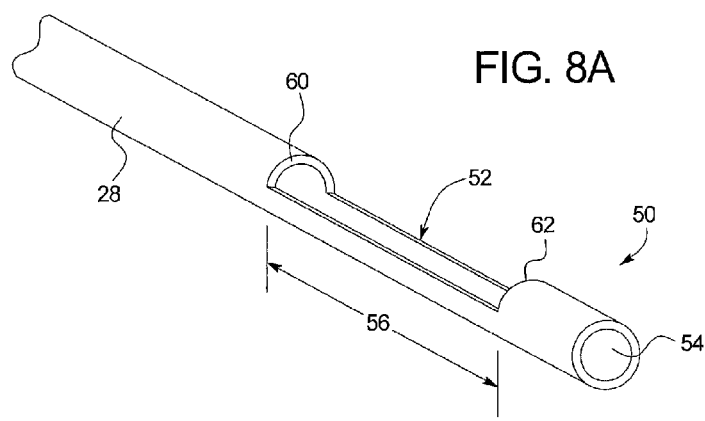
FIGS. 8A and 8B show an embodiment of movement restriction mechanism located at a proximal end of the introducer of FIGS. 3 and 4.
Figure 8B:
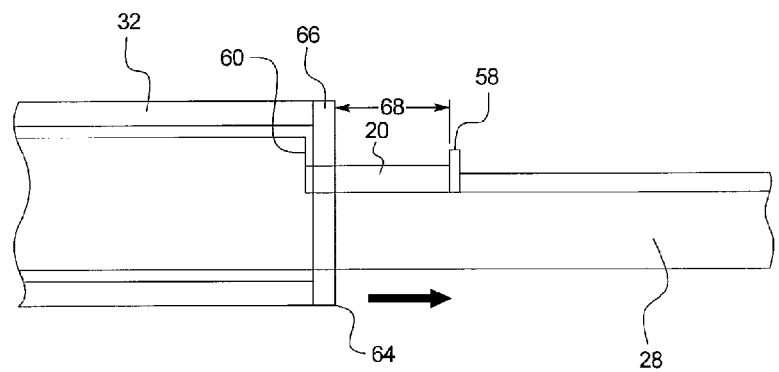
Figure 9:
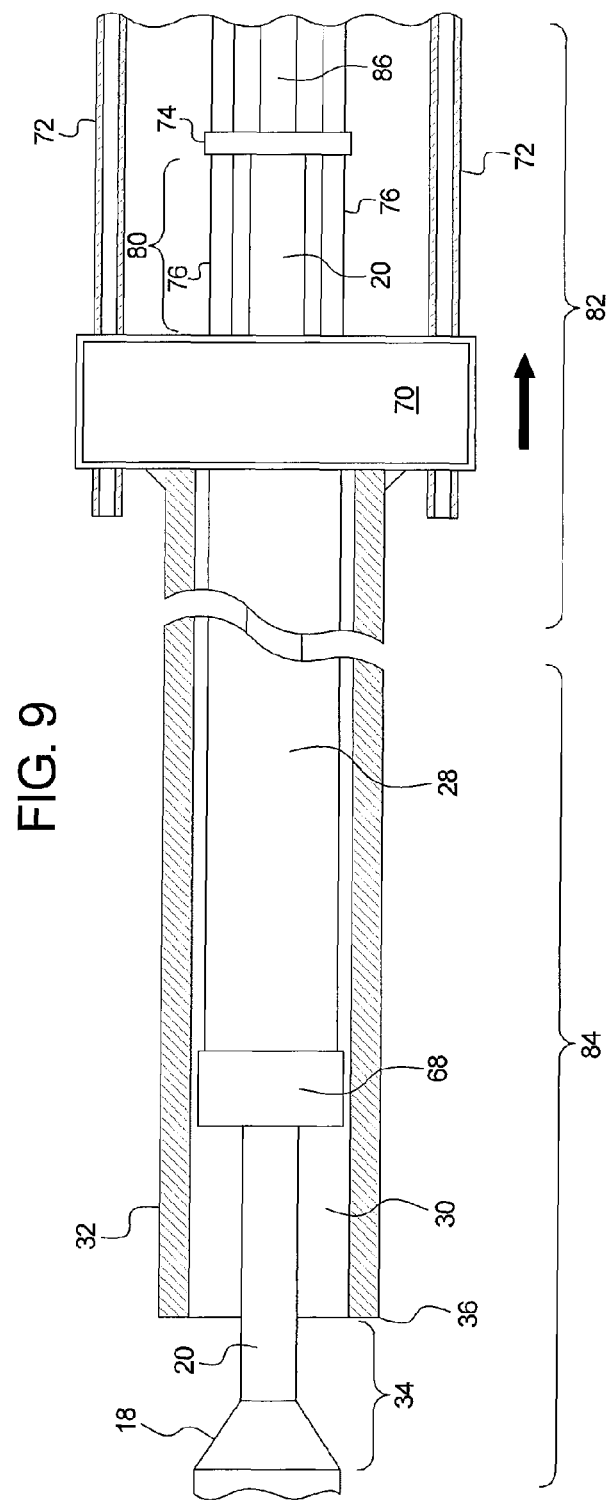
FIG. 9 shows another embodiment of restriction mechanism for the introducer of FIGS. 3 and 4.

FIGS. 8A, 8B and 9 show some examples of mechanism for limiting the amount by which the sheath 32 can be retracted relative to the guide wire catheter 20 and dilator tip 18, that is to limit the size of the gap 34. These mechanisms are located at the proximal end of the introducer 40, that is at the end which remains external to the patient. It will be appreciated from a consideration of FIGS. 3 and 4 in particular that the distal end of the introducer 40 includes no additional components for limiting the movement of the sheath 32, with the result that the introducer 40 will retain all of the important characteristics of pushability and trackability of conventional introducers, that is the flexibility required to be able to move through the tortuous vasculature of a patients vessels.

Referring first to FIG. 8A, there is shown the proximal end of the pusher element 28 of the embodiment of FIGS. 3 and 4.

This proximal end 50 of the pusher element 28 is typically located outside of a patient, within an external manipulation section of the introducer 40.

At the proximal end 50, the pusher element 28 includes a cut out slot 52 which provides access to the interior lumen 54 of the pusher element 28. The slot has a length 56 which is preferably around the same length as the length of the implantable medical device carried on the introducer 40. The slot 52 may be slightly shorter or slightly longer than the implantable medical device in some implementations.

Referring now to FIG. 8B, there is shown a part of the proximal end of the introducer 40 with the pusher element 28, the sheath 32 and the guide wire catheter 20 assembled together. Guide wire catheter 20 resides within the pusher element 28 and is able to move within the lumen 54 of the pusher element 28. The proximal end of the guide wire catheter 20 is provided with a flange 58 which extends out of the slot 52 of the pusher element 28 and which is of a size enabling it to abut against the side walls 60, 62 of the slot 52. The sleeve 32 has a proximal end 64 which includes a depending flange 66 which extends into the zone of the slot 52 of the pusher element 28 and sufficiently far as to extend radially inwards relative to the flange 58 of the guide wire catheter 20.

It will be seen in FIG. 8B that the guide wire catheter 20 and in particular the portion up to the flange 58 extends by a distance 68 beyond the end 64 of the sheath 32. This distance 68 represents the gap 34 which is created at the distal end of the introducer 40 and shown in FIG. 4. This is explained in more detail below.

The sheath 32 is retractable in the direction of the arrow shown in FIG. 8B to the proximal end of the introducer 40, in so doing moving from the covering position shown in FIG. 3 towards the open position shown in FIG. 4. As the sheath 32 is retracted, it slides over the pusher element 28 and the guide wire catheter 20, until the flange 66 at the proximal end 64 of the sheath 32 comes into contact with the flange 58 of the guide wire catheter 20. At this point, the sheath 52 has moved sufficiently to open up the gap 34 shown in FIG. 4. Further retraction of the sheath 32 pulls with it also the guide wire catheter 20 in a proximal direction. This has the effect of moving the distal end 68 of the pusher element 28 forwards thereby in effect reducing the space 30 within the sheath 32 and within which the medical device is located (seen better in FIG. 4). This forward movement of the pusher element 28 has the effect of pushing the medical device 26 out of the space 30, through the gap 34 and thus of progressively deploying the medical device 26 as the sheath 32 continues to be retracted in the direction of the arrow of FIG. 8B. The sheath 32 can be pulled in the proximal direction until the flange 58 of the guide wire catheter 20 comes up against and abuts the proximal end wall 62 of the slot 52, which brings the flange 66 of the sheath 32 to a stop also. At this point, the sheath 32 has moved backwards by the distance 56 (less the thickness of the flanges 58 and 66) and thus by a sufficient amount to provide for complete deployment of the medical device 26 from within the holding space 30 at the distal end of the sheath 32. It will be appreciated that for the entirety of the movement of the guide wire catheter 20 along the slots 52, the annular gap 34 at the distal end of the introducer remains the same.

Referring now to FIG. 9, there is shown another embodiment of mechanism for limiting the movement of the sheath 32 relative to the dilator tip 18. FIG. 9 shows a major portion of the introducer 40, including the proximal end of the dilator 18.

In this embodiment, the sheath 32 is fixed to a slider 70, which is located on guide rails 72, along which it is able to slide. The guide wire catheter 20 is itself fixed to its own slider 74, which is located on its own respective guide rails 76. It will be seen in FIG. 9 that the sliders 70 and 74 are separated from one another by a distance 80, which is equivalent to the gap 34 which in use is opened at the distal end 36 of the assembly 40. It will be appreciated that FIG. 9 shows the proximal end 82 of the assembly in a configuration which would occur when the outer sheath 32 is in the closed configuration, whereas the distal end 84 is shown in an open configuration, when the annular gap 34 has been created.

It will also be appreciated that the proximal mechanism 70-80 will typically be housed within a suitable casing.

In use, when the slider 70 is pulled backwards, in a proximal direction, it will cause the sheath 32 to retract also, thereby opening the gap 34, until the slider 70 comes into abutment with the slider 74. At this stage, the sheath 32 and guide wire catheter 20 (and hence also the dilator tip 18) will move in unison, thereby keeping the gap 34 constant. As the sliders 70, 74 are moved together further in the proximal direction, both the sheath 32 and the dilator tip 18 move backwardly in unison relative to the distal end 68 of the pusher element 28, thereby to effect the withdrawal of the implantable medical device 26 from within the holding zone 30. For this purpose, there is provided an arrangement to ensure movement of pusher element 28 relative to the sheath 32 and the guide wire catheter 20, which in this example includes an inner catheter or cannula 86 which is coupled to the pusher element 28 to ensure that this remains stationary as the sheath and guide wire cannula 20 are withdrawn in a proximal direction to effect deployment of the medical device 26 carried on the introducer.

The skilled person will appreciate that many other mechanisms could be used for effecting the relative movements of the sheath 32, dilator tip 18 and pusher element 28 and that these are all within the abilities of the skilled person. As explained, this mechanism should be retained at the proximal end of the introducer 40 so as to keep the distal end (seen in FIGS. 3 to 7) free of any elements of the mechanism, which could adversely affect the characteristics of the distal end of the introducer.

It will be appreciated in particular with respect of the embodiments of the mechanism of FIGS. 8A, 8B and 9 that there would also be provided the relevant seals for sealing the interior spaces of the introducer assembly to reduce or prevent blood or other fluid leakage from the patient. These are all elements are common place in the art and are therefore not described herein.

What is claimed is:

1. An introducer assembly for use in an endoluminal deployment of an implantable medical device, the assembly including a distal end and a proximal end; an elongate carrier element including a distal end and a proximal end and being operable to carry a medical device at or proximate its distal end; an elongate sheath operable to cover the carrier element and the medical device thereon, and a pusher element slidably disposed between the carrier element and the sheath and abutting an end of the medical device, wherein the sheath is movable by a sliding action from a covering position covering the medical device carried on the introducer assembly to a deployment position in which the medical device can be released from the introducer assembly, an annular gap thereby being disposed between the sheath and the carrier element in the deployment position, the annular gap extending less than the length of a holding zone for the medical device; and a restriction mechanism operable to restrict an amount of movement of the sheath relative to the carrier element such that, after the sheath moves relative to the carrier element to form the annular gap, the distal end of the carrier element and a distal end of the sheath are simultaneously withdrawn thereafter relative to the pusher element as the medical device expands through the annular gap, a width of the annular gap thereby remaining constant as the sheath and the carrier element are retracted together relative to the medical device, the restriction mechanism being located at or proximate the proximal end of the carrier element and a proximal end of the sheath that remain external to a patient; and wherein the restriction mechanism includes a slide and follower coupled to a respective one of the carrier element and the sheath, the slide having a limited range of travel, at the end of which further sliding of the sheath relative to the carrier element is prevented.

2. An introducer assembly according to claim 1, wherein the carrier element is a guide wire catheter.

3. An introducer assembly according to claim 1, wherein the assembly includes a dilator tip at the distal end of the carrier element, the annular gap in the deployment position being disposed between the dilator tip and the distal end of the sheath.

4. An introducer assembly according to claim 3, wherein the annular gap is operable to generate friction on the medical device during its deployment.

5. An introducer assembly according to claim 4, wherein the annular gap to be opened at the distal end of the sheath has a width substantially the same as or slightly smaller than a thickness of the medical device carried on the introducer.

6. An introducer assembly according to claim 1, wherein the slide is in the form of a slot.

7. An introducer assembly according to claim 1, wherein the slide is in the form of a guide rod.

8. An introducer assembly according to claim 1, wherein the annular gap to be opened at the distal end of the sheath has a width substantially the same as or slightly smaller than a thickness of the medical device carried on the introducer.

9. An introducer assembly according to claim 1, wherein a radial spacing between the carrier element and sheath is the same as or greater than the width of the annular gap.

10. An introducer assembly according to claim 1, wherein the annular gap between the sheath and the carrier element is slightly less than a thickness of the medical device carried on the introducer, the medical device thereby contacting surfaces of the sheath and the carrier element to generate friction on the medical device during its deployment.

11. An introducer assembly according to claim 1, wherein the carrier element is located within a lumen of the pusher element.

12. An introducer assembly according to claim 1, wherein the carrier element is a guide wire catheter, the assembly includes a dilator tip
at the distal end of the carrier element, the annular gap in the deployment position being disposed between the dilator tip and the distal end of the sheath, and the carrier element is located within a lumen of the pusher element.

13. An introducer assembly according to claim 12, wherein the annular gap to be opened at the distal end of the sheath has a width substantially the same as or slightly smaller than a thickness of the medical device carried on the introducer.

14. An introducer assembly according to claim 13, wherein a radial spacing between the carrier element and sheath is the same as or greater than the width of the annular gap.

15. An introducer assembly according to claim 14, wherein the annular gap is operable to generate friction on the medical device during its deployment.

16. An introducer assembly according to claim 15, wherein the slide is in the form of a slot.

17. An introducer assembly according to claim 15, wherein the slide is in the form of a guide rod.

18. An introducer assembly according to claim 1, wherein the annular gap to be opened at the distal end of the sheath has a width which is greater than a thickness of the medical device carried on the introducer.

19. An introducer assembly accordingly claim 1, wherein the follower comprises a first flange coupled to the carrier element.

20. An introducer assembly according to claim 19, wherein the slide comprises a second flange coupled to a proximal end of the sheath and extending radially inward.

21. An introducer assembly according to claim 20, wherein when the sheath is in the deployment position, the first flange abuts against the second flange.

22. An introducer assembly according to claim 19, wherein a slot is formed on a surface of the pusher element, and the first flange extends out of the slot.

23. An introducer assembly according to claim 1, wherein the follower comprises a first slider coupled to the carrier element and movable on a first guide rail.

24. An introducer assembly according to claim 23, wherein the slide comprises a second slider coupled to the sheath and movable on a second guide rail.

25. An introducer assembly according to claim 24, wherein when the sheath is in the deployment position, the first slider abuts against the second slider.

26. An introducer assembly for use in an endoluminal deployment of an implantable medical device, the assembly including a distal end and a proximal end; an elongate carrier element including a distal end and a proximal end and being operable to carry a medical device at or proximate its distal end; an elongate sheath operable to cover the carrier element and the medical device thereon, and a pusher element slidably disposed between the carrier element and the sheath and abutting an end of the medical device, wherein the sheath is movable by a sliding action from a covering position covering the medical device carried on the introducer assembly to a deployment position in which the medical device can be released from the introducer assembly, an annular gap thereby being disposed between the sheath and the carrier element in the deployment position, the annular gap extending less than the length of a holding zone for the medical device; and a restriction mechanism operable to restrict an amount of movement of the sheath relative to the carrier element such that, after the sheath moves relative to the carrier element to form the annular gap, the distal end of the carrier element a distal end of the sheath are simultaneously withdrawn thereafter relative to the pusher element as the medical device expands through the annular gap, a width of the annular gap thereby remaining constant as the sheath and the carrier element are retracted together relative to the medical device, the restriction mechanism being located at or proximate the proximal end of the carrier element and a proximal end of the sheath that remain external to a patient; and wherein the restriction mechanism includes a slide and follower coupled to a respective one of the carrier element and the sheath, the slide and the follower having a limited range of travel relative to each other, at the end of which further travel of the sheath relative to the carrier element is prevented.

27. An introducer assembly accordingly claim 26, wherein the follower comprises a first flange coupled to the carrier element.

28. An introducer assembly according to claim 27, wherein the slide comprises a second flange coupled to a proximal end of the sheath and extending radially inward.

29. An introducer assembly according to claim 28, wherein when the sheath is in the deployment position, the first flange abuts against the second flange.

30. An introducer assembly according to claim 27, wherein a slot is formed on a surface of the pusher element, and the first flange extends out of the slot.

31. An introducer assembly according to claim 26, wherein the follower comprises a first slider coupled to the carrier element and movable on a first guide rail.

32. An introducer assembly according to claim 31, wherein the slide comprises a second slider coupled to the sheath and movable on a second guide rail.

33. An introducer assembly according to claim 32, wherein when the sheath is in the deployment position, the first slider abuts against the second slider.

* * * * *